(12) United States Patent
Ruedisueli et al.

(10) Patent No.: US 6,611,151 B1
(45) Date of Patent: Aug. 26, 2003

(54) COATING ASSESSMENT SYSTEM BASED ON ELECTROCHEMICAL NOISE

(75) Inventors: Robert L. Ruedisueli, Vienna, VA (US); Christine A. Bowles, Ellicott City, MD (US); Brian D. Layer, Gaithersburg, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/900,872

(22) Filed: Jul. 10, 2001

Related U.S. Application Data

(60) Provisional application No. 60/234,214, filed on Sep. 21, 2000.

(51) Int. Cl.[7] ............................................. G01R 27/08
(52) U.S. Cl. ........................................................ 324/700
(58) Field of Search ................................ 324/699, 700, 324/709, 690; 422/53; 205/776.5, 777, 791, 791.5, 793.5, 794; 204/404, 406, 228.6, 228.7, 228.9, 229.1

(56) References Cited

U.S. PATENT DOCUMENTS

| | | | |
|---|---|---|---|
| 4,045,647 A | * 8/1977 | Thome | 219/121 EB |
| 4,221,651 A | 9/1980 | Mansfeld et al. | 204/412 |
| 4,575,678 A | 3/1986 | Hladky | 205/776 |
| 4,806,849 A | 2/1989 | Kihira et al. | 324/700 |
| 5,093,626 A | 3/1992 | Baer et al. | 324/671 |
| 5,236,564 A | 8/1993 | Berg et al. | 204/488 |
| 5,373,734 A | 12/1994 | Shih et al. | 73/105 R |
| 5,425,867 A | * 6/1995 | Dawson et al. | 204/400 |
| 5,746,905 A | 5/1998 | Murray | 205/791 |
| 5,888,374 A | * 3/1999 | Pope et al. | 205/775.5 |
| 6,054,038 A | * 4/2000 | Davis et al. | 205/776.5 |
| 6,280,603 B1 | * 8/2001 | Jovancicevic | 205/775.5 |

OTHER PUBLICATIONS

Brian D. Layer, "The Uses of Electrochemical Noise in the Evaluation of Coating Condition," 19–page high school science project report displayed at the science fair which took place at the Poolesville High School science fair on Jan. 15, 2000 in Poolesville, Maryland. Please note: A copy of this document is not provided herewith but is provided at "Appendix A" of the application.

Mary Zoccola, "Science and Engineering Apprentice Program Helps Division and Students," *Wavelengths:* An Employee Digest of Events and Information, Navel Surface Warfare Center, Carderock Division, 9500 MacArthur Boulevard, West Bethesda, Maryland 20817–5700, April 2000, pp 22 and 24.

(List continued on next page.)

*Primary Examiner*—Safet Metjahic
*Assistant Examiner*—Etienne P LeRoux
(74) *Attorney, Agent, or Firm*—Howard Kaiser

(57) ABSTRACT

Apparatus for using electrochemical noise analysis to assess the coating upon a conductive substrate comprises an electrolyte-containing cell, a witness electrode, a reference electrode and a working conductor. The electrolyte-containing cell is securely coupled with the coated conductive substrate so that the electrolyte is contiguous with a coated area of the metal substrate, which is demarcated by an electrolytic contact-permitting aperture in the electrolyte-containing cell. The witness electrode contacts the electrolyte and connects to an ammeter. The reference electrode contacts the electrolyte and connects to a voltmeter. Via the working conductor, the ammeter and the voltmeter each connect to a noncoated region of the metal substrate. The conductive substrate's coated area which contacts the electrolyte effectively represents a working electrode. Practice "in the field" is possible relative to coated conductive substrates associated with diverse entities.

31 Claims, 8 Drawing Sheets

OTHER PUBLICATIONS

G. L. Edgemon (Lockheed Martin Hanford Corp., Richland, WA) and G.E.C. Bell (M.J. Schiff & Associates, Inc., Claremont, CA), "Technical Basis for Electrochemical Noise Based Corrosion Monitoring of Underground Nuclear Waste Storage Tanks," WHC–SD–WM–TI–772, Rev. 0, http://www.hanford.gov/twrs/corrosion/772web/wmti772.htm (22 pp, printed out on Jun. 20, 2001).

Robert Cottis and Stephen Turgoose, *Electrochemical Impedance and Noise (Corrosion Testing Made Easy)*, NACE International, 1440 South Creek Drive, Houston, Texas 77084, 1999, Chapter 1, pp. 1–7.

John N. Murray, "Evaluation of Electrochemical Noise to Monitor Corrosion for Double Hull Applications," Technical Report, Naval Surface Warfare Center, Carderock Division, CARDIVNSWC–TR–61–94/29, Aug. 1994.

Gordon P. Bierwagen, Carol S. Jeffcoate, Junping Li, Seva Balbyshv, Dennis E. Tallman, Douglas J. Mills, "The Use of Electrochemical Noise Methods (ENM) to Study Thick, High Impedance Coatings," *Progress in Organic Coatings* 29, 1996, pp. 21–29.

Colin J. Sandwith and Robert L. Ruedisueli, Corrosion and Aging Tests—Via Measurements of Insulation Resistance, Impedance, and Electrochemical Noise—on Jackets of Small–Diameter, Armored, Fiber–Optic Cables with and without Simulated Biofouling Damage, *Proceedings of the Ocean Community Conference 1998*, Marine Technology Society, Baltimore, Maryland, Nov. 16–19, 1998, pp 393–397.

Gretchen A. Jacobson, Managing Editor, "Corrosion Control," *Materials and Performance*, Jan. 2000, pp 22–27.

Jeffrey R. Kearns, John R. Scully, Pierre R. Roberge, David L Reichert, John L. Dawson, Eds., "Forward" (1 p), "Contents" (3 pp), "Overview" (pp ix–xvii) *Electrochemical Noise Management for Corrosion Applications*, ASTM, 100 Barr Harbor Drive, West Conshohocken, Pennsylvania, ASTM Publication Code No. 04–012770–27, First International Symposium on Electrochemical Noise Measurement for Corrosion Applications, Montreal, Quebec, Canada, May 15–16, 1994.

David L. Reichert, "Electrochemical Noise Measurement for Determining Corrosion Rates," *Electrochemical Noise Measurement for Corrosion Applications*, Jeffrey R. Kearns, John R. Scully, Pierre R. Roberge, David L. Reichert, John L. Dawson, Eds., ASTM, 100 Barr Harbor Drive, West Conshohocken, Pennsylvania, ASTM Publication Code No. 04–012770–27, First International Symposium on Electrochemical Noise Measurement for Corrosion Applications, Montreal, Quebec, Canada, May 15–16, 1994, pp 79–89.

Gordon P. Bierwagen, Douglas J. Mills, Dennis E. Tallman, Brian S. Skerry, "Reproducibility of Electrochemical Noise Data from Coated Metal Systems," *Electrochemical Noise Measurement for Corrosion Applications*, Jeffrey R. Kearns, John R. Scully, Pierre R. Roberge, David L. Reichert, John L. Dawson, Eds., ASTM, 100 Bar Harbor Drive, West Conshohocken, Pennsylvania, ASTM Publication Code No. 04–012770–27, First International Symposium on Electrochemical Noise Measurement for Corrosion Applications, Montreal, Quebec, Canada, May 15–16, 1994, pp 427–445.

John N. Murray, "Electrochemical Test Methods for Evaluating Organic Coatings on Metals: An update. Part I, Introduction and Generalities Regarding Electrochemical Testing of Organic Coatings," Reprinted from *Progress in Organic Coatings* 30, 1997, pp 225–233.

John N. Murray, "Electrochemical Test Methods for Evaluating Organic Coatings on Metals: An update. Part III. Multiple Test Parameter Measurements," Reprinted from *Progress in Organic Coatings* 31, 1997, pp 375–391. Please note: P. 388 (15th p.) is missing from the appended copy.

Gordon Bierwagen, Douglas J. Mills, "Characterization of Corrosion under Marine Coatings by Electrochemical Noise Methods," Final Report for the period Sep. 1, 1992–Aug. 30, 1994, Grant No. N 00014–93–1–0013, The Office of Naval Research, 800 N. Quincy Street, Arlington, Virginia 22217–5660 (61 pp plus cover page, errata page).

F. Mansfeld, L.T. Han, C.C. Lee, "Analysis of Electrochemical Noise Data for Polymer Coated Steel in the Time and Frequency Domains," *J. Electrochem. Soc.*, Vol. 143, No. 12, Dec. 1996, pp L286–L289.

Gordon Bierwaen, Junping Li, Seva Balbyshev, Jason Lindquist, "Electrochemical Noise Methods Applied to the Study of Organic Coatings," Final Office of Naval Research Report, Grant No. N00014–95–1–0507, Jul. 2000, Department of Polymers & Coatings and Department of Chemistry, North Dakota State University, Fargo, North Dakota 58105 (191 pp.)

S. Mabbutt, D.J. Mills, "Review of Work at UCN Using Electrochemical Noise Method (ECN) to Assess Anti–Corrosive Coatings," paper presented at Eurocorr 2000 conference, London, United Kingdom, Sep. 11–14, 2000 (10 pp.).

* cited by examiner

COATING ASSESSMENT SYSTEM BASED ON ELECTROCHEMICAL NOISE

CROSS-REFERENCE TO RELATED APPLICATION

This application claims the benefit of U.S. Provisional Patent Application No. 60/234,214 filed Sep. 21, 2000, entitled "In Situ Coating Assessment System Based on Electrochemical Noise," joint inventors Robert L. Ruedisueli, Christine A. Bowles and Brian D. Layer, incorporated herein by reference.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to methods and apparatuses for evaluating conditions of coatings on metallic substrates, more particularly to such methods and apparatuses involving electrochemical noise.

Electrochemical impedance spectroscopy (EIS) is an electrochemical methodology in which an ac signal (typically, a small voltage signal) is applied to an electrode (e.g., a corroding metal) and the response is measured. The current-time and the voltage-time measurements are processed to provide a representation of the ac impedance at different frequencies, known as the "impedance spectrum."

The term "impedance" is the ac analogue of dc resistance. The relationship for dc is given by Ohm's law, $V=IR$, wherein V (e.g., in volts) is the voltage across a resistor R (e.g., in ohms) and I (e.g., in amps) is the current. Similarly, the relationship for ac is given by $V=IZ$, wherein Z is the impedance of the circuit. Unlike resistance R, impedance Z may depend on the frequency f (e.g., in hertz, which is the number of cycles per second) of the applied ac signal.

Two parameters which relate the output current to the input voltage define the impedance of a system at a given frequency. The first parameter is the amplitude of the ac current divided by the amplitude of the ac voltage. The second parameter is the phase angle, which is proportional to the shift in time between peak current and peak voltage. The impedance spectrum comprises an accumulation of values of these parameters for various frequencies.

In the past teen to twenty years, electrochemical impedance spectroscopy (EIS) has become widely accepted as a nondestructive technique for evaluating the electrochemical properties of non-conductive coatings applied to metallic substrates. EIS data (such as maximum impedance, $Z_{max}$) have been successfully equated to given coating conditions. For example, a $Z_{max}$ value of $10^9$–$10^{11}$ ohms-cm$^2$ indicates a 'good' coating while a $Z_{max}$ value less than $10^6$ ohms-cm$^2$ indicates a 'bad' coating.

U.S. Navy researchers have used EIS in the laboratory to characterize and evaluate many organic coating systems on metallic substrates for long periods (up to 10 years) of exposure to saltwater. Due to the logistics of the test method, however, it is not practical to perform EIS testing in the field to evaluate the condition of coatings on ships and vehicles. While EIS can be performed in the field, it requires a relatively large amount of time to perform each test, and the data are somewhat complicated. Efforts to make in-field EIS testing more logistically feasible have shown varying degrees of success, but the lack of straightforward, easy-to-interpret output from EIS tests remains a hindrance to the widespread use of EIS testing as a monitoring technique in the field.

Electrochemical noise (ECN), also referred to as electrochemical noise analysis (ENA) or electrochemical noise measurement/method(s) (ENM), is a nondestructive analysis technique in which the direct, current "noise" and voltage "noise" associated with electrochemical reactions on a metallic surface are each measured and recorded. The meaning of the word "noise" in the context of ECN is distinguishable from its commonly understood meaning, wherein the word "noise" refers to unwanted sound. Electrochemical noise does not involve audible sounds (i.e., fluctuations in air pressure or acoustic noise), but rather is concerned with fluctuations in electrochemical potential and electrochemical current. Electrochemical potential noise is the fluctuation in the electrochemical potential of an electrode relative to a reference electrode. Electrochemical current noise is the fluctuation in an electrochemical current.

Generally, measurement of ECN involves the utilization of three test electrodes. For instance, two steel electrodes are connected to an ampmeter, and current therebetween is recorded; one of the two steel electrodes and a reference electrode are connected to a voltmeter, and voltage therebetween is recorded. Although only one of the two steel electrodes is connected to the voltage meter, the two steel electrodes effectively behave as a single electrode of twice the area, since the ammeter used to measure current is assumed to behave ideally (i.e., measuring current with no voltage drop). While the three test electrodes are immersed in a salt solution, two kinds of "time records" are effectuated, viz., current-against-time (variation of current with time) and potential-against-time (variation of electode potential with time).

ECN testing has been used in the past ten years to evaluate the kinetics of localized electrochemical reactions and processes, such as pitting reactions on passive alloys. EIS has been much more commonly effectuated than has ECN for evaluating coating conditions. More recently, ECN has been gaining interest as a technique for evaluating coatings, albeit that EIS testing remains the more "tried-and-true," traditional approach for such purposes.

For instructive discussion regarding EIS and ECS in relation to the electrochemistry of corroding metal samples, see Robert Cottis and Stephen Turgoose, Electrochemical Impedance and Noise (Corrosion Testing Made Easy), NACE International, 1440 South Creek Drive, Houston, Tex. 77084, 1999, incorporated herein by reference; see, especially, Chapter 1, pages 1–7.

Also incorporated herein by reference are the following articles: John N. Murray, "Evaluation of Electrochemical Noise to Monitor Corrosion for Double Hull Applications," Technical Report, Naval Surface Warfare Center, Carderock Division, CARDIVNSWC-TR-61-94/29, August 1994; Gordon P. Bierwagen, Carol S. Jeffcoate, Junping Li, Seva Balbyshev, Dennis E. Tallman, Dougals J. Mills, "The Use of Electrochemical Noise Methods (ENM) to Study Thick, High Impedance Coatings," *Progress in Organic Coatings* 29, 1996, pp 21–29; Colin J. Sandwith and Robert L. Ruedisueli, "Corrosion and Aging Tests—Via Measurements of Insulation Resistance, Impedance, and Electrochemical Noise—on Jackets of Small-Diameter, Armored, Fiber-Optic Cables with and without Simulated Biofouling Damage,". *Proceedings of the Ocean Community Conference* 1998, Marine Technology Society, Baltimore, Md., Nov. 16–19, 1998, pp393–397; Gretchen A. Jacobson; Managing Editor, "Corrosion Control," Materials Performance, January 2000, pp 22–27; Jeffery R. Kearns, John R. Scully, Pierre R. Roberge; David L. Reichert, John L. Dawson, Eds., "Overview," pp ix–xvii, Electrochemical Noise Measurement for Corrosion Applications, ASTM, 100 Barr Harbor Drive, West Conshohocken, Pa., ASTM Publication Code No. 04-012770-27, First International Symposium on Electrochemical Noise Measurement for Corrosion Applications, Montreal, Quebec, Canada, May 15–16, 1994; David L. Reichert, "Electrochemical Noise Measurement for Determining Corrosion Rates," *Electrochemical Noise Measurement for Corrosion Applications*, Jeffery R. Kearns, John R. Scully, Pierre R. Roberge, David L. Reichert, John L. Dawson, Eds., ASTM, 100 Barr Harbor Drive, West Conshohocken, Pa., ASTM Publication Code No. 04-012770-27, First International Symposium on Electrochemical Noise Measurement for Corrosion Applications, Montreal, Quebec, Canada, May 15–16, 1994, pp 79–89; Gordon P. Bierwagen, Douglas J. Mills, Dennis E. Tallman, Brian S. Skerry, "Reproducibility of Electrochemical Noise Data from Coated Metal Systems," *Electrochemical Noise Measurement for Corrosion Applications*, Jeffery R. Kearns, John R. Scully, Pierre R. Roberge, David L. Reichert, John L. Dawson, Eds., ASTM, 100 Barr Harbor Drive, West Conshohocken, Pa., ASTM Publication Code No. 04-012770-27, First International Symposium on Electrochemical Noise Measurement for Corrosion Applications, Montreal, Quebec, Canada, May 15–16, 1994, pp 427–445; John N. Murray, "Electrochemical Test Methods for Evaluating Organic Coatings on Metals: An update. Part I. Introduction and Generalities Regarding Electrochemical Testing of Organic Coatings," Reprinted from *Progress in Organic Coatings* 30, 1997, pp 225–233; John N. Murray, "Electrochemical Test Methods for Evaluating Organic Coatings on Metals: An update. Part III. Multiple Test Parameter Measurements," Reprinted from *Progress in Organic Coatings* 31, 1997, pp 375–391; Gordon Bierwagen, Douglas J. Mills, "Characterization of Corrosion under Marine Coatings by Electrochemical Noise Methods," Final Report for the period Sep. 1, 1992–Aug. 30, 1994, Grant Number N 00014-93-1-0013, The Office of Naval Research, 800 N. Quincy Street, Arlington, Va. 22217-5660 (61 pp plus cover page, errata page); F. Mansfeld, L. T. Han, C. C. Lee, "Analysis of Electrochemical Noise Data for Polymer Coated Steel in the Time and Frequency Domains," *J. Electrochem. Soc.*, Vol. 143, No. 12, December 1996, pp L286–L289; Gordon Bierwaen, Junping Li, Seva Balbyshev, Jason Lindquist, "Electrochemical Noise Methods Applied to the Study of Organic Coatings," Final Office of Naval Research Report, Grant No. N00014-95-1-0507, July 2000, Department of Polymers & Coatings and Department of Chemistry, North Dakota State University, Fargo, N.Dak. 58105 (191 pages).

Further incorporated herein by reference are the following United States patents: Pope et al. U.S. Pat. No. 5,888,374 issued Mar. 30, 1999; Murray U.S. Pat. No. 5,746,905 issued May 5, 1998; Shih et al. U.S. Pat. No. 5,373,734 issued Dec. 20, 1994; Berg et al. U.S. Pat. No. 5,236,564 issued Aug. 17, 1993; Baer et al. U.S. Pat. No. 5,093,626 issued Mar. 3, 1992; Kihira et al. U.S. Pat. No. 4,806,849 issued Feb. 21, 1989; Hladky U.S. Pat. No. 4,575,678 issued Mar. 11, 1986; Mansfeld et al. U.S. Pat. No. 4,221,651 issued Sep. 9, 1980.

SUMMARY OF THE INVENTION

In view of the foregoing, it is an object of the present invention to provide method and apparatus for performing on-site (e.g., in-field or in-service) evaluations of coatings on metallic substrates.

The present invention provides a device, system and method for evaluating coating condition using electrochemical noise (ECN) and a "witness" (e.g., steel or platinum) specimen. According to this invention, the witness specimen is a bare (uncoated) electrode and contacts (e.g., is immersed in) the same (identically contained) electrolyte solution as do a standard "reference" electrode and the coated metallic substrate (such as a coated test panel, a tank wall area or a ship'hull area), thus obviating the need for a conventional "salt bridge" between plural discretely contained electrolyte quantities.

In accordance with many embodiments of the present invention, coating assessment apparatus is provided which is suitable for on-site use in association with a coated metal substrate and with electrochemical noise instrumentation including an ammeter (which measures current) and a voltmeter (which measures voltage). The inventive apparatus comprises a receptacle, a witness electrode, a reference electrode and lead means. The receptacle is for containing electrolyte and for being coupled with the coated metal substrate whereby the electrolyte contacts the coated metal substrate. The witness electrode is for contacting the electrolyte and for connecting to the ammeter. The reference electrode is for contacting the electrolyte and for connecting to the voltmeter. The lead means is for connecting a metal portion of the coated metal substrate to the ammeter and the voltmeter.

Further provided by many embodiments of the present invention is a system, based on electrochemical noise, for evaluating the condition of a coating on a metallic substrate. The inventive system comprises an ammeter, a voltmeter, an electrolyte reservoir, a witness electrode, a reference electrode, a first conductor, a second conductor and a third conductor. The electrolyte reservoir is attachable to the metallic substrate whereby the electrolyte communicates with the metallic substrate. The witness electrode is contactable with the electrolyte (e.g., communicable with a liquid electrolyte-containing sponge-like member placed inside the reservoir; or, immersible in the reservoir which contains free-standing liquid electrolyte). The reference electrode is contactable with the electrolyte (e.g., communicable with a liquid electrolyte-containing sponge-like member placed inside the reservoir; or, immersible in the reservoir which contains free-standing liquid electrolyte). The first conductor is for connecting the metallic substrate with the ammeter and with to the voltmeter. The second conductor is for connecting the witness electrode with the ammeter. The third conductor is for connecting the reference electrode with the voltmeter.

Also provided by many embodiments of the present invention is a method, based on electrochemical noise, for evaluating the condition of a coating on a metallic substrate. The inventive method comprises the steps of: attaching an electrolyte reservoir to the metallic substrate whereby the electrolyte communicates with the metallic substrate; causing a witness electrode to contact the electrolyte (e.g., immersing the witness electrode in the electrolyte reservoir; or, causing the witness electrode to touch a sponge-like member placed inside the reservoir); causing a reference electrode to contact the electrolyte (e.g., immersing the reference electrode in the electrolyte reservoir; or, causing the reference electrode to touch a sponge-like member placed inside the reservoir); electrically connecting the metallic substrate with an ammeter and with a voltmeter; electrically connecting the witness electrode with the ammeter; and, electrically connecting the reference electrode with the voltmeter.

In accordance with typical embodiments of the present invention, a device for using electrochemical noise analysis for purposes of assessing the coating upon a conductive (e.g., metal) substrate comprises an electrolyte-containing vessel, a witness electrode,sa reference electrode and a working conductor. The electrolyte-containing vessel is adaptable to being firmly coupled with the coated conductive substrate so that the electrolyte is adjacent to a coated region of the metal substrate located inside the electrolyte-containing vessel. The witness electrode is contactable with (e.g., immersible in) the electrolyte and is adaptable to being connected to an ammeter. The reference electrode is contactable with (e.g., immersible in) the electrolyte and is adaptable to being connected to a voltmeter. The working conductor is adaptable to connecting the ammeter and the voltmeter to a noncoated region of the metal substrate located outside the electrolyte-containing vessel.

In inventive principle, the region of the coated conductive substrate which is contacting the electrolyte and is bounded by an electrolytic contact-permitting opening in the electrolyte-containing vessel is effectively rendered a working electrode. In situ application can be propitiously afforded by fixing and sealing the bottom of the device with respect to a coated conductive substrate such as would be part of a marine or nonmarine transportation vehicle or a tank wall. If the vessel is infused with free-standing liquid electrolyte, a top seal is preferably provided. If an electrolyte-soaked sponge or foam member is disposed within the vessel, a top seal may be optional.

Inventive practice will normally prescribe that the same electrolytic entity (e.g., a liquid electrolyte-saturated sponge disposed inside a cell; or, a body of electrolyte liquid contained by a cell) will be in contact with the witness electrode, the reference electrode and the coated metallic substrate test region (e.g., the portion of the metallic substrate which is bordered by the perimeter of the base opening of the cell and is adjacent to the electrolytic entity).

According to typical inventive embodiments, a generally cylindrical electrolyte reservoir (such as includes a vessel, container, chamber, receptacle, cell, etc.) is capable of being coupled with the coated metallic substrate so that the electrolyte is contiguous with the coated metallic substrate through the open lower end of the reservoir. A first conductor means is situated outside the reservoir and connects an uncoated portion of the metallic substrate (e.g., a bare spot, a projection or a stud) to an ammeter and a voltmeter; that is, the first conductor means is in electrical contact with the uncoated metallic substrate portion, and with the ammeter, and with the voltmeter. A second conductor means passes through the upper end of the reservoir and connects the witness electrode to the ammeter; that is, the second conductor means is in electrical contact with the witness electrode and with the ammeter. A third conductor means passes through the upper end of the reservoir and connects the reference electrode to the voltmeter; that is, the third conductor means is in electrical contact with the reference electrode and with the voltmeter. The coated metallic substrate portion which is in electrical contact with the electrolyte and is inside the periphery of the lower open end of the reservoir functionally represents the working electrode; in other words, this electrically connected (coated) metallic substrate portion effectively acts as a working electrode.

According to many inventive embodiments, the chamber will be provided with a first opening means (including at least one opening) for allowing the leads to enter the chamber, and a second opening means (including at least one opening) for allowing the electrodes to contact the substrate. Typically, the first opening means (for permitting lead entry) and the second opening means (for permitting electrode contact) will be located at generally or approximately opposite extremes of the chamber. As an example, if a cap-seal-type sealing device is implemented for sealing the chamber at its lead-entry end, the cap-seal should be appropriately apertured with one or more openings for accommodating the passing therethrough of the leads; for instance, according to some embodiments a cap-seal has two small holes for correspondingly accommodating the passing therethrough of two leads.

This invention can be practiced in the field (e.g., on ships) to evaluate coating condition. Furthermore, the data obtained using the inventive sensor and method have been demonstrated by the inventors to correlate well with data obtained unsing electrochemical impedance spectroscopy (EIS). It is noted that the U.S. Navy bases its databases pertaining to long-term coating performance on, inter alia, EIS methodology. The U.S. Navy also bases such databases on salt fog spray chamber tests, field exposure tests, visual evaluations, scratch and prohesion. Based on inventive testing, in situ (e.g., in-the-field, or in-service) coating assessments effectuated using inventive ECN sensors are demonstrably relatable to EIS laboratory databases, and may be relatable to other databases, as well.

The present invention uniquely features the performance of ECN tests between a coated steel specimen and a bare steel specimen, which serves as a probe or "witness" specimen. This inventive ECN approach offers numerous advantages not only over conventional ECN approaches but also over conventional EIS approaches. ECN offers a logistically feasible means of evaluating coating condition in the field, with shorter test times than EIS and with test output that is more straightforward and easier to interpret than EIS data. However, long-term ECN databases on Naval and Department of Defense (DoD) coatings do not exist. By correlating EIS and ECN data, ECN offers a practical means of bridging the gap between laboratory-based data bases and in-situ, condition-based monitoring in the field. The correlation of data from the two techniques (EIS and ECN) offers practical and useful benefits for the evaluation of coating condition and prediction of coating life.

As described herein (including in Appendix A), the inventors investigated a practical methodology for correlating test results of the inventive ECN sensor and procedure with electrochemical impedance spectroscopy (EIS) data. This investigation was conducted at the Naval Surface Warfare Center, Carderock Division (NSWCCD) located in West Bethesda, Md.

ECN measurements obtained using the inventive method can serve as a practical link between existing coatings data bases (which are based on samples tested using EIS throughout long periods of exposure) and inventively acquired data pertaining to in-service coatings performance on ships and vehicles. ECN data from the apparatus and method according to this invention can be correlated with existing EIS data in order to demonstrate that ECN can quantitatively distinguish between "good" coatings and "bad" coatings. The inventors have demonstrated the ability of the inventive ECN system to quantitatively differentiate between 'good' and 'bad' coatings, and thus have as demonstrated the feasibility of using the inventive ECN system to quantitatively probe the condition of ships and vehicles in the field and predict coating life based on existing data bases.

Other objects, advantages and features of this invention will become apparent from the following detailed description of the invention when considered in conjunction with the accompanying drawings.

BRIEF DESCRIPTION OF THE APPENDICES

The following appendices are hereby made a part of this disclosure:

Attached hereto marked APPENDIX A and incorporated herein by reference is the following 19-page high school science project report, authored by joint inventor Brian D. Layer, which discloses various aspects of the present invention: Brian D. Layer, "The Uses of Electrochemical Noise in the Evaluation of Coating Condition," displayed at the science fair which took place at the Poolesville High School science fair on Jan. 15, 2000 in Poolesville Md.

BRIEF DESCRIPTION OF THE DRAWINGS

In order that the present invention may be clearly understood, it will now be described, by way of example, with reference to the accompanying drawings, wherein like numbers indicate the same or similar components, and wherein.

DETAILED DESCRIPTION OF THE INVENTION

In order to establish correlativeness of data obtained from EIS and ECN tests, two pairs of coated steel test specimens, both of which were included in the long-term EIS coatings database, were evaluated. The first pair consisted of two, "bad" specimens which had consistently shown low EIS impedance values and shown visual evidence of degradation in the form of heavy rust. The second pair consisted of "good" samples with high impedance values and no visual evidence of coating failure.

Figure 1:
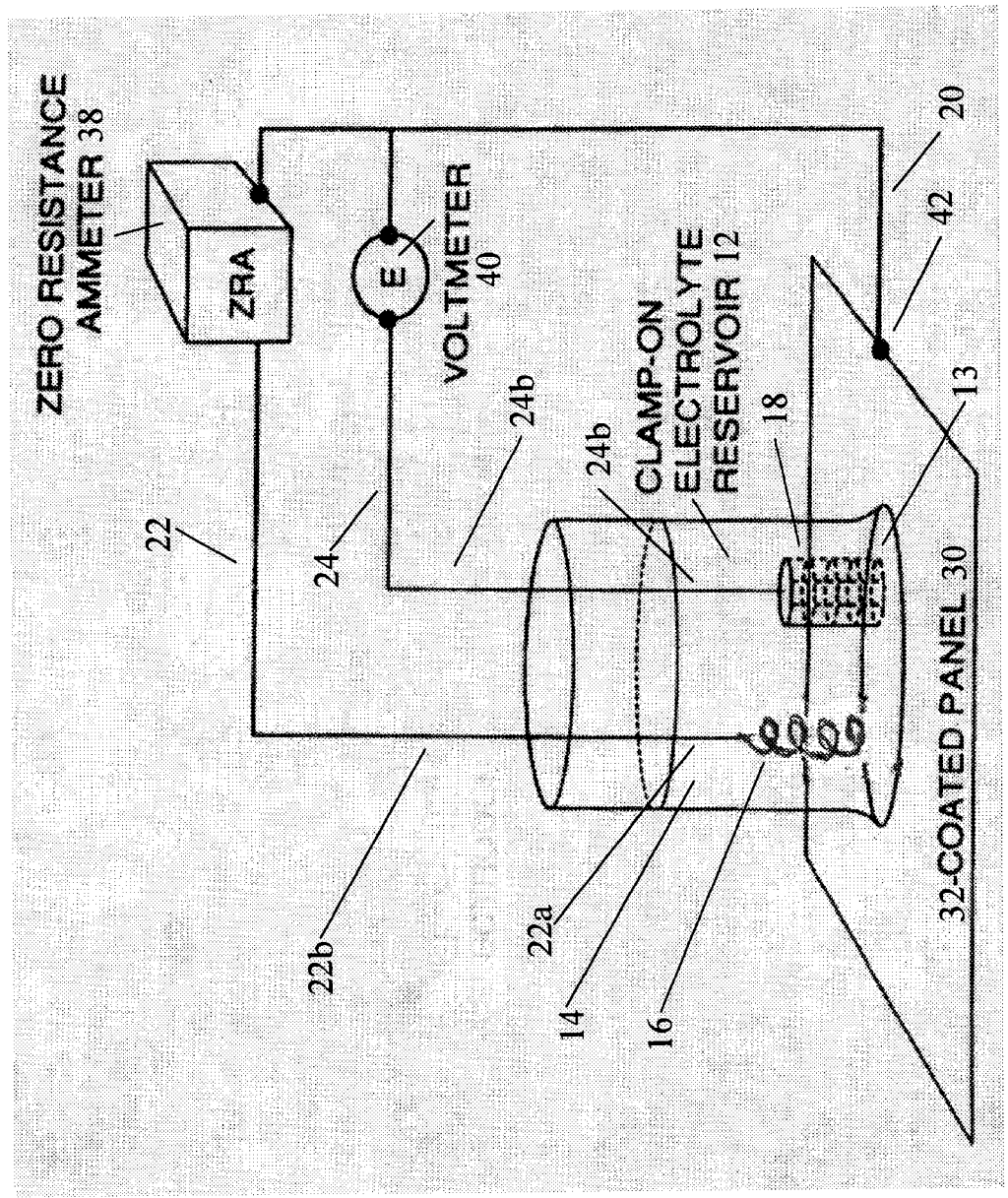
FIG. 1 is a diagrammatic perspective view of the prototypical embodiment, used in testing conducted by the U.S. Navy, of an ECN sensor in accordance with the present invention.

ECN tests were performed in a conventional way, implementing an electrolyte bridge ("salt bridge"), on each pair of samples ("good" and "bad" pairs), and the resultant data were compared with EIS data previously obtained for each individual sample; for an instructive representation of a classical laboratory experimental ECN set-up such as used in this conventional ECN testing, see "FIG. 1" in the aforementioned U.S. Navy technical report John N. Murray, "Evaluation of Electrochemical Noise to Monitor Corrosion for Double Hull Applications," Technical Report, Naval Surface Warfare Center, Carderock Division, CARDIVNSWC-TR-61-94/29, August 1994.

In addition to performing conventional ECN tests on pairs of coated steel specimens, the inventors performed inventive ECN tests. Referring now to the figures herein, in accordance with the present invention, testing was performed between bare steel "witness" specimens and coated specimens representing the "good" and "bad" conditions. According to the present invention's prototypical test methodology, the steel "witness" specimens served as ECN probes for evaluating the condition of the coated specimens; a separate set of similar inventive experiments was conducted using bare platinum "witness" specimens.

ECN tests were inventively performed using the prototype inventive ECN device illustrated in FIG. 1. Since the bare carbon steel (or platinum) witness specimen (witness electrode 16) was immersed in the same test solution as the coated panel (32-coated metallic substrate 30), this eliminated the need for a salt bridge. The inventive ECN device 10 embodiments depicted in FIG. 2 through FIG. 5 are similar to that shown in FIG. 1. Among the inventive features shown in FIG. 2 through FIG. 6 which foster suitability for in situ implementation in association with coatings such as on ship hulls or tank walls are: top sealability means; bottom sealability means; and, bottom attachability/detachability means (such as via magnetic attraction for magnetic substrates, or suction or adhesive for non-magnetic substrates) with respect to a metallic substrate.

The feasibility of the present invention was demonstrated by the experimental analysis which was conducted utilizing the inventive prototype portrayed in FIG. 1. Implementing an inventive ECN sensor 10 such as shown in FIG. 1, ECN measurements were taken between "witness" specimens (witness electrodes 16) consisting of bare steel or bare platinum (representing the substrate material of a ship hull) and the "good" and "bad" coated steel specimens (metal substrates 30 coated with coating 32) representing good and bad areas of a coating on a ship's hull or tank wall.

Figure 5:
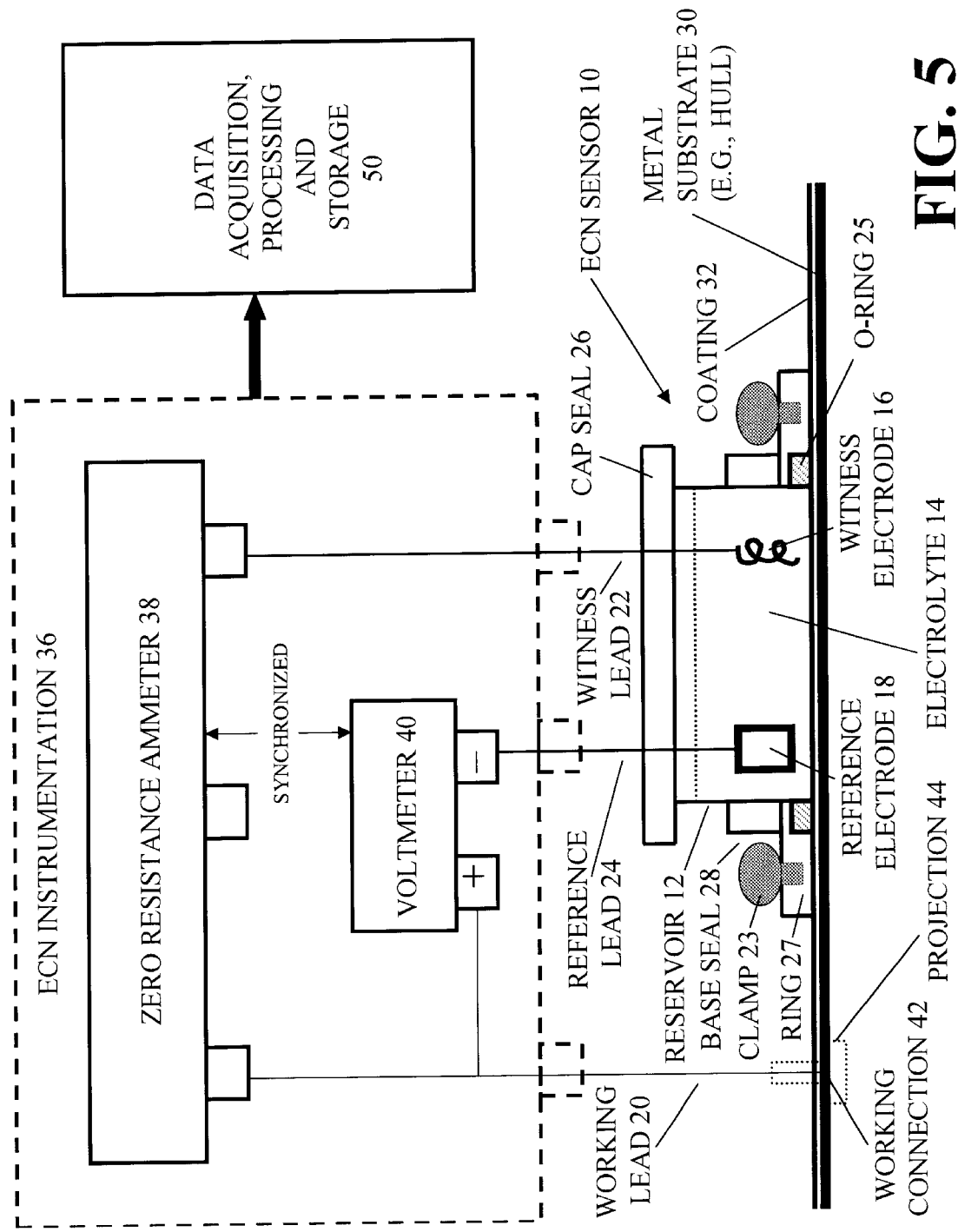
FIG. 5 is a schematic and block diagrammatic representation of an embodiment of an ECN system in accordance with the present invention.

Thus, by using an inventive monitoring system such as shown in FIG. 5, wherein a "witness" specimen (witness electrode 16) represents the substrate material of interest, the condition of a coating 32 in service can be inventively evaluated quantitatively using ECN. Furthermore, by inventively correlating the ECN data obtained in this manner with existing EIS databases, meaningful and reliable predictions of coating life will be possible.

Figure 3:
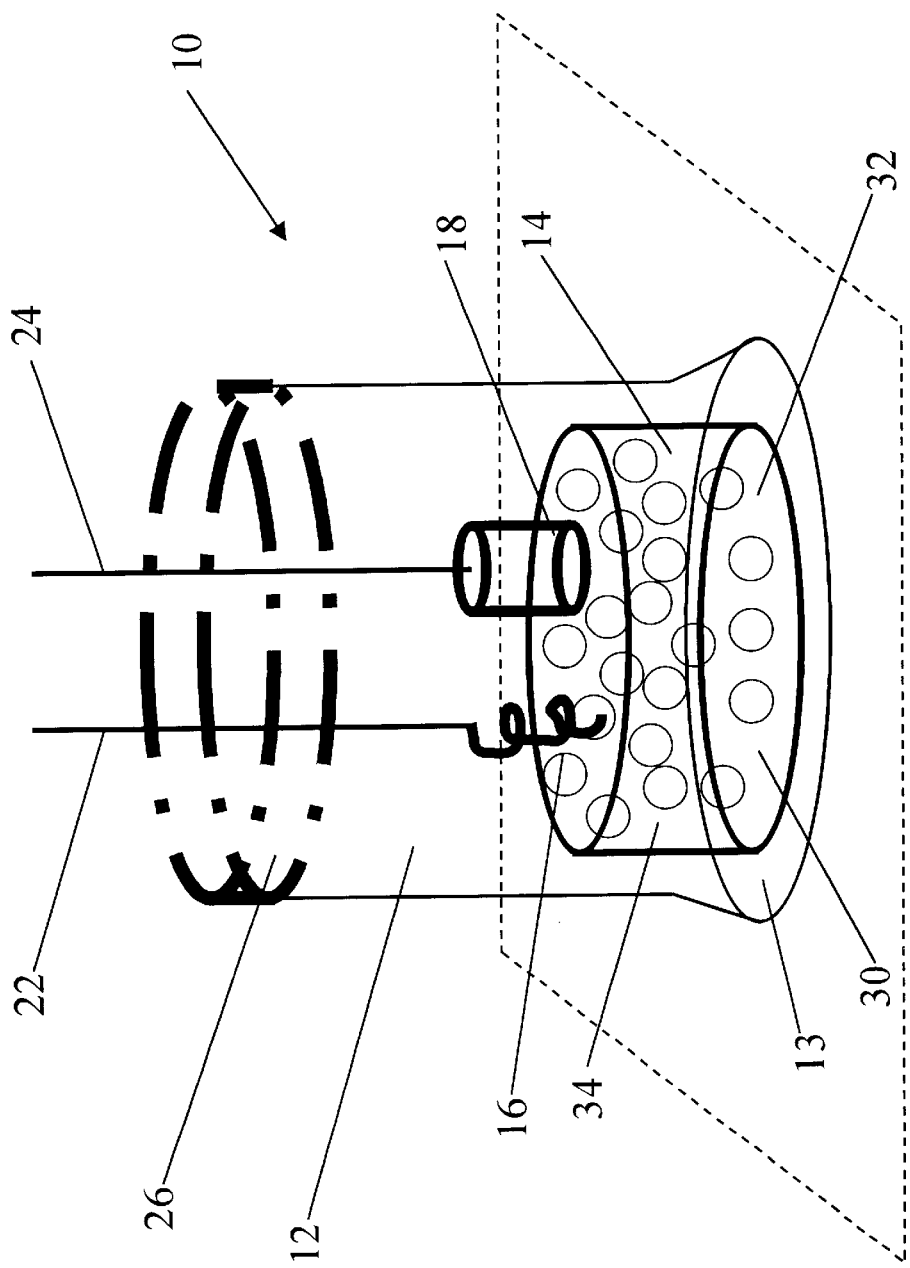
FIG. 3 is a diagrammatic perspective view of an embodiment of an ECN sensor in accordance with the present invention, particularly illustrating a sponge-containing electrolyte reservoir.
Figure 4:
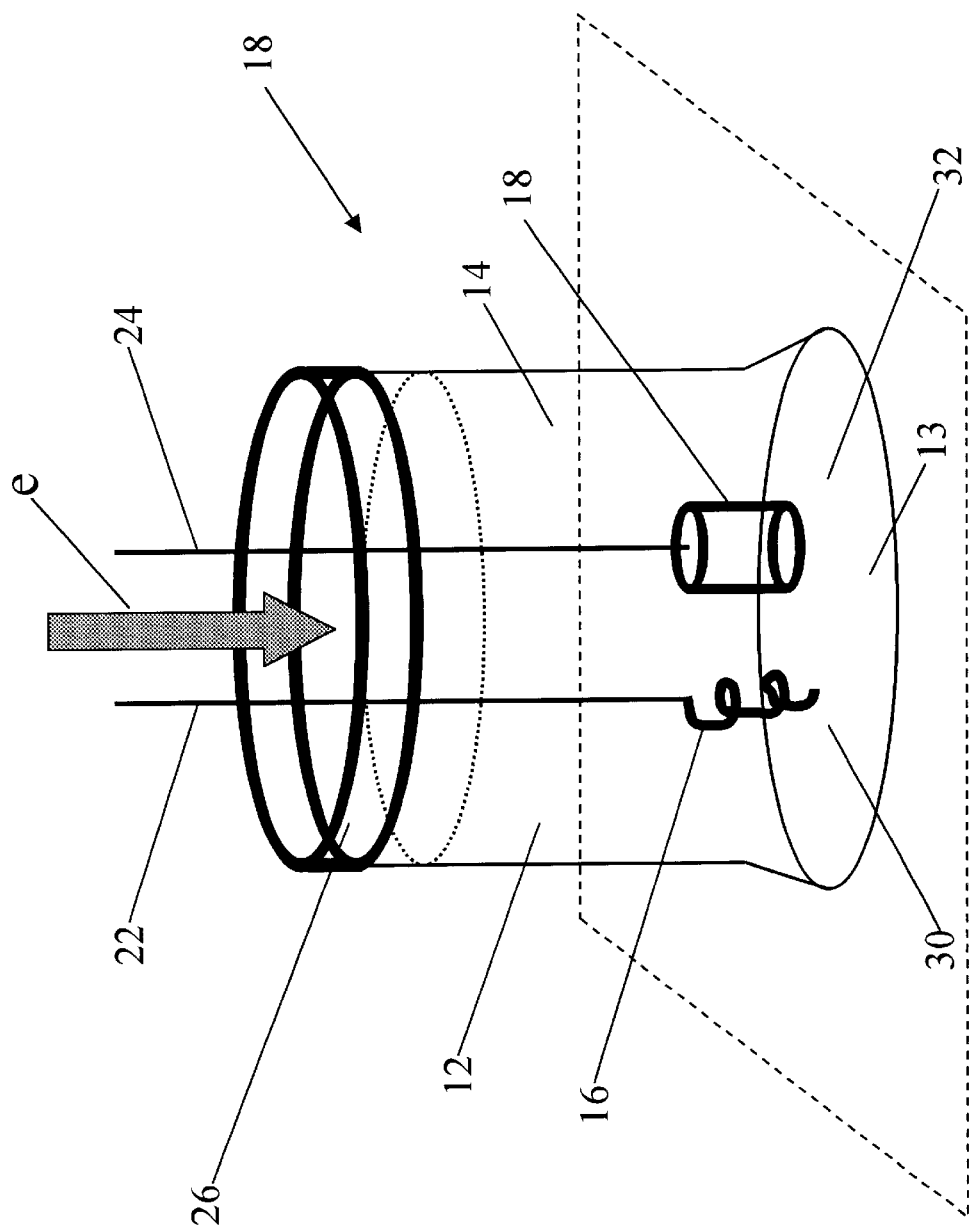
FIG. 4 is a diagrammatic perspective view of another embodiment of an ECN sensor in accordance with the present invention, particularly illustrating an injectable electrolyte reservoir.
Figure 6:
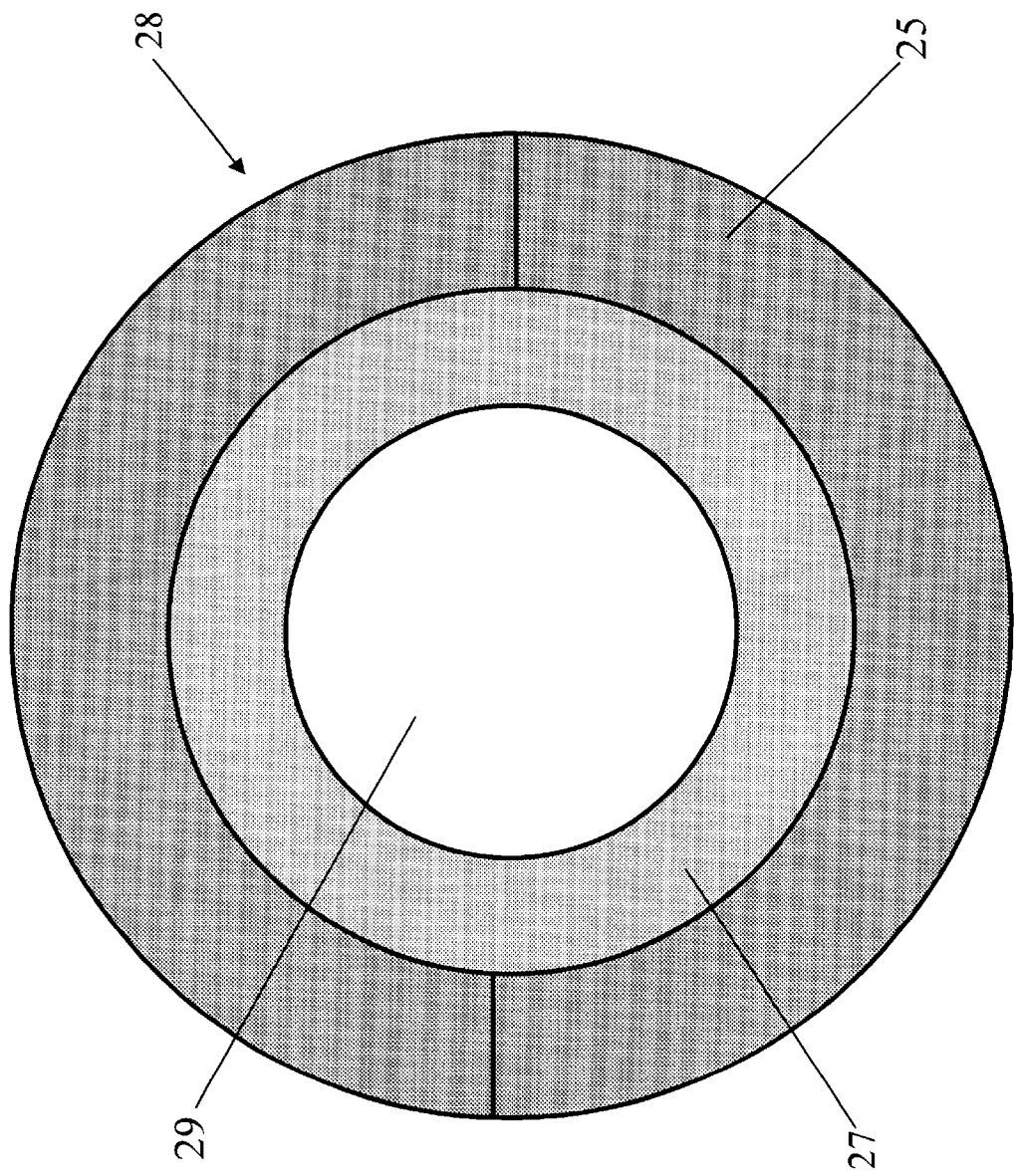
FIG. 6 is a diagrammatic bottom plan view of a magnetic hold-down ring/seal assembly for sealing and securing the electrolyte reservoir with respect to the coated metal substrate.

An inventive ECN test system comprising a "witness" probe and appropriate instrumentation can be used in the field to monitor the condition of a coating such as paint on the hull of a ship, the wall of a tank, or the body of a vehicle. As shown in FIG. 3, a saturated sponge 34 (made of sponge, foam or other porous or open cell material) can contain the necessary electrolyte 14. As shown in FIG. 4, liquid electrolyte can be introduced through the top of cell 12, which would previously or subsequently be capped. FIG. 5 shows an inventive ECN setup for in situ monitoring a ship's hull or other coated entity. As shown in FIG. 5 and FIG. 6, the inventive ECN cell 12 is held to the surface of the 32-coated metal substrate (e.g., hull) 30 via a magnetic ring/seal assembly 25.

With reference to FIG. 1 through FIG. 6, inventive ECN device 10 includes electrolyte reservoir 12, liquid electrolyte 14, witness electrode 16, reference electrode 18, working lead 20, witness lead 22 and reference lead 24. Top cap-seal 26, sponge 34 and/or bottom magnetic hold-down ring/seal assembly 28 are also included in many inventive embodiments. As illustrated in FIG. 1 through FIG. 5, ECN testing is being inventively performed in relation to a conductive substrate 30, typically a conductive metal/metallic substrate 30, which is provided with a coating 32.

Electrolyte reservoir 12 is a clamp-on, seal-to-surface, cylindrical cell structure which is partially or substantially filled with liquid electrolyte 14. Reservoir 12 is fixedly mounted upon 32-coated metallic substrate 30 using a magnetic clamping base sealing and coupling device such as hold-down ring/seal assembly 28, shown in FIG. 5 and FIG. 6, having clamp fasteners/tighteners 23, a flanged (e.g., split) magnetic clamp ring 25, an o-ring-type seal 27 and a central hole 29 compatible with the circumference of reservoir 12. The magnetic attraction of ring 25 of hold-down ring/seal assembly 28 to metal substrate 30-helps to fix reservoir 12 in relation to 32-coated metal substrate 30.

Many substrates of large structures are magnetic (typically, made of steel). However, in accordance with this invention, nonmagnetic adherence means (e.g., adhesive, suction or another mounting or "clamping" technique) can additionally or alternatively be used in order to stably-affix reservoir 12 to non-magnetic 32-coated metallic substrate 30. Stainless steel, aluminum, copper, etc. are examples of non-magnetic conductive substrate materials.

Reservoir 12 as shown in FIG. 1 is representative of the inventive cell which was used in inventive laboratory tests on single coated panels. FIG. 2 through FIG. 6 portray an inventive arrangement 10 including reservoir 12 which is suitable not only for in-laboratory ECN single panel 30 testing of out-of-service coatings 32 but also for on-site, ECN single panel 30 field testing of in-service coatings 32. Inventive device 10 is endowed with certain features e.g., top cap-seal 26, sponge 34 and/or bottom magnetic hold-down ring/seal assembly 28—which promote on-site adaptability such as in relation to a ship's hull or a tank wall.

Once reservoir 12 is appropriately securely situated atop coating 32 of metallic substrate 30, electrolyte 14 can be caused to be contained by reservoir 12 according to various inventive techniques, such as elaborated upon hereinbelow. For instance, electrolyte 14 liquid can be injected into a sealed reservoir 12 after being placed on 32-coated metal substrate 30 (e.g., hull or wall). Or, electrolyte 14 liquid can be contained within a sponge or foam structure 34 situated inside an open reservoir 12 cell before or after placement on 32-coated metal substrate 30.

As shown in FIG. 3, sponge 34 is a porous absorbent member (such as characterized by a sponge-like or foam-like structure) which is at least substantially saturated with electrolyte 14 and is inserted in reservoir 12. A cap-seal 26 can be removable and securely replaceable (e.g., like a medicine bottle cap) for purposes of introducing and withdrawing contents (such as electrolyte 14-soaked sponge 34) therein and therefrom. According to some inventive embodiments utilizing an electrolyte 14-soaked sponge 34, the upper end of reservoir 12 can be left open during operation of inventive ECN device 10, thus obviating telexed altogether for sealing means such as cap-seal 26 at the top end of reservoir 14.

As shown by vertical arrow e in FIG. 4, electrolyte 14 is fluidly inserted through the top end of reservoir 12. For instance, electrolyte 14 can be injected in liquid form through an opening in the cap-seal 26 of reservoir 12. Alternatively, cap-seal 26 can be removed, electrolyte 14 poured into reservoir 12, and cap-seal 26 replaced. Alternatively, cap-seal 26 can be made of a membranous (e.g., rubber) material which is impermeable to electrolyte 14 but which is permeable to a hypodermic syringe-type device usable for injecting electrolyte 14 therethrough.

Witness electrode 16, reference electrode 18 and 32-coated metallic substrate 30 each must contact electrolyte 14 during inventive operation of ECN device 10. For this purpose, reservoir 12 is at least partially open at the bottom end. A round opening 13, approximately concentric with the circumference of reservoir 12, is provided at the bottom end of reservoir 12 for promoting communication between electrolyte 14 and 32-coated metallic substrate 30.

As illustrated in FIG. 3, approximately cylindrical sponge 14, diametrically slightly or somewhat smaller than the circular bottom opening 13 of reservoir 12, sits atop coating 32 of metal substrate 30 at the bottom of reservoir 12 approximately coaxially therewith. Witness electrode 16 and reference electrode 18 are each touching the top flat surface of electrolyte 34-soaked sponge 34, and coating 32 is touching the bottom flat surface of sponge 34. Alternatively, to ensure good contact, witness electrode 16 and reference electrode 18 can be "sleeved" snugly into electrolyte 34-soaked sponge 34.

Neither opening 13 nor sponge 34 need be circularly or cylindrically shaped in inventive practice; preferably, however, opening 13 accommodates sponge 34, and sponge 34 includes a flat lower surface portion adaptable to contiguity with 32-coated metallic substrate 30. In fact, it is readily apparent to the ordinarily skilled artisan who reads this disclosure that, in inventive practice, reservoir 12 can be any of diverse kinds of containers, vessels, receptacles, etc., and need not have a cylindrical or near cylindrical shape. Any reservoir 12 shape will due which advances the inventive principles of (i) electrolyte containment, (ii) electrolyte contiguity (in relation to the subject coated metal substrate), (iii) base fixability (in relation to the subject coated metal substrate) and (iv) base sealability (in relation to the subject coated metal substrate). Glass, plastic or other nonconductive (preferably transparent) materials are suitable for the material composition of reservoir 12.

In accordance with the inventive electronic arrangement, the metallic substrate 30 itself constitutes, in effect, the "working electrode" of inventive ECN device 10. That is, the working electrode is the portion of conductive substrate 30 (e.g., metal panel, ship's hull or tank wall) which lies beneath the coating 32 area being tested—more specifically, the portion of the coating which contacts the electrolyte 14 and is circumscribed by the electrolytically vehicular opening 13 of reservoir 12.

Witness electrode 16, made of steel in inventive testing but preferably made of platinum or other noble metal, is supported within reservoir 12 on witness lead 22, which serves as the electrical connection means from witness electrode 16 to ECN instrumentation 36. Reference electrode 18 is made of a standard electrochemical (half-cell) reference material (such as silver-silver chloride) and is similarly supported by reference lead 24. Reference lead 24 similarly serves as the electrical connection means from reference electrode 18 to ECN instrumentation 36.

Figure 2:
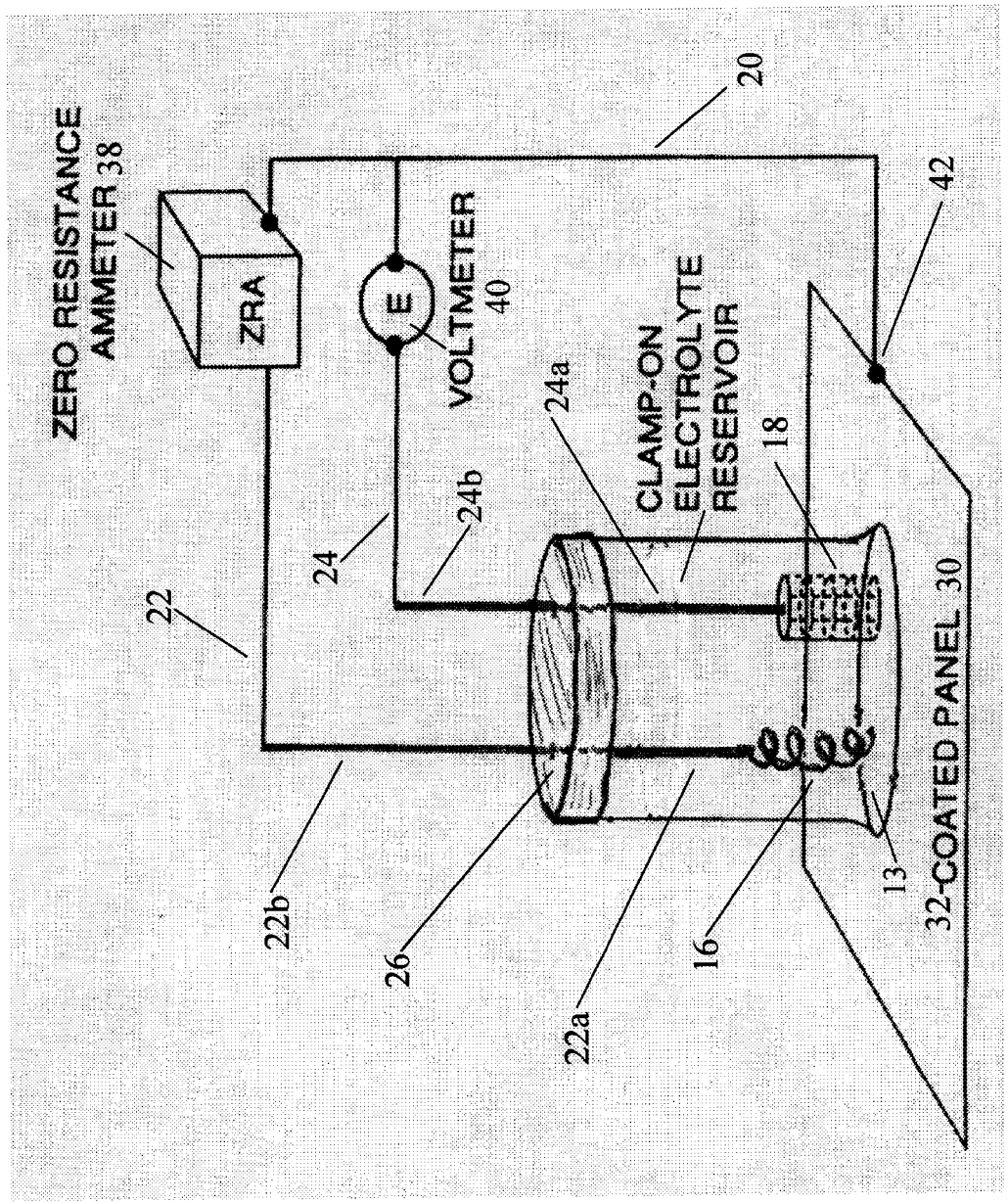
FIG. 2 is a diagrammatic perspective view, similar to the view shown in FIG. 1, of an embodiment of an ECN sensor in accordance with the present invention, particularly illustrating a cap seal. The inventive embodiments depicted in FIG. 2 through FIG. 5 are similar to the inventive prototype shown in FIG. 1, but are especially suitable for in situ utilization in association with coatings on ship hulls or tank walls.

According to typical inventive practice, the lower end sections of witness lead 22 and reference lead 24 (which are connected to witness electrode 16 and reference electrode 18, respectively) are each a rigid, insulated, conductive shaft or a heavy gauge wire. Referring to FIG. 1 and FIG. 2, these lower extreme portions, witness lead portion 22a and reference lead portion 24a (which are connected to witness electrode 16 and reference electrode 18, respectively) should each be of sufficient length to clear the top of reservoir 12, at which point conventional insulated (e.g., copper) wire lead 22b and lead 24b portions correspondingly connected thereto can serve to complete the corresponding connections to ECN instrumentation 36 (in particular, to ammeter 38 and voltmeter 40, respectively).

Reference is now made particularly to FIG. 1, FIG. 2 and FIG. 5. Witness electrode 16 is connected, via witness lead 22, to ammeter (e.g., a zero resistance ammeter, or ZRA) 38. Reference electrode 18 is connected, via reference lead 24, to voltmeter 40 (e.g., an electrometer). Metallic substrate 30 is connected, via working lead 20, to both ammeter 38 and voltmeter 40. Witness lead 20 is the insulated wire conductor which effects connection between ammeter 38 and the witness electrode 16 metal (e.g., platinum) in reservoir (e.g., cell) 12. Reference lead 24 is the conductor which effects connection between voltmeter 40 and reference electrode 18. Working lead 20 is the conductor which effects connection between the test subject coating's metal substrate 30 (electrically conductive ship's hull, tank wall or other structural member) and ECN instrumentation 36 (which includes ammeter 38 and voltmeter 40).

It is notable that, according to many embodiments of the inventive configuration: Witness electrode 16 is directly connected to ammeter 38; reference electrode 18 is directly connected to voltmeter 40; and, metallic substrate 30 is directly connected to ammeter 38 and voltmeter 40. That is, conspicuously absent in the inventive circuitry are any electronic elements (such as series resistors) between witness electrode 16 and ammeter 36, as well as between reference electrode 18 and voltmeter 38, as well as between metallic substrate 30 and either ammeter 36 or voltmeter 38.

Connection of working lead 20 to metallic substrate 30 at working connection 42 will normally be more easily accomplished in the laboratory than in the field. In a laboratory, the inventive practitioner can grind off a small section of the coating (e.g., paint) 32 on the test panel substrate 30, and then clip working lead 20 to the working connection 42 location in the test panel substrate 30 using an alligator clip or similar means. In the field (e.g., on a ship), a connection between working lead 20 and metallic substrate 30 can be made at an uncoated surface working connection 42 location in metallic substrate 30, such as a bare (uncoated) spot, a projection (e.g., lug) or a fastener (e.g, stud 44 shown in FIG. 5). Typically, lugs (e.g., for hatch covers) or studs or other types of hardware are imbedded in a ship's hull or tank wall. In a worst case scenario, the inventive practitioner would have to grind through the coating 32 (e.g., paint) in a small area (or plural small areas if the test domain is very large), effecting a connection at the "de-coated" area through a conductive adhesive or gel analogous to what may be used when electrocardiogram (ECG) electrodes are connected to a person.

As shown in FIG. 5, the working connection 42 point is somewhat distanced or removed (typically a few or several inches, if not several feet or more, in inventive in situ applications) from the inventive ECN sensor 10 test site. Working lead 20, when connected at working connection 42, effectuates an actual electrical connection between ECN instrumentation 36 and the metal substrate 30 which lies under coating 32. Working connection 42 serves to render the portion of metal substrate 30 which is in the vicinity of working connection 42 at the same electrical potential as the portion of metal substrate 30 which lies beneath coating 32 within the test cell perimeter (e.g., the circumference of circular opening 13 at the bottom end of generally cylindrical reservoir 12 shown in FIG. 1 through FIG. 5).

According to frequent inventive practice, working lead 20, witness lead 22 and reference lead 24 are preferably shielded to eliminate "noise" other than ECN in reservoir 12. Moreover, working lead 20 and reference lead 24 can preferably each be provided with "dual connections" or "sensing" capability in order to eliminate IR from voltage measurements. For instance, working lead 20 will actually comprise two "sub-leads" (not separately shown) running together, viz., a working electrode sublead (the function of which is to conduct electronic signals from metal substrate 30 to ECN instrumentation 36) and a "working sense" sublead (the.function of which is to measure and cancel the voltage drop along the working electrode sublead). In typical inventive practice, both the working electrode sublead and the working sense sublead should be shielded to minimize unwanted electrical noise pick-up (such as may derive from overhead lights).

FIG. 5 illustrates that a computer system 50 comprising data processing, signal processing, data acquisition and/or information storage can be connected to ECN instrumentation 36. Aforementioned U.S. Pat. No. 5,888,374 to Pope et al. is instructive regarding principles of computer monitoring such as would be inventively practicable in association with inventive ECN device 10. In the light of this disclosure, the ordinarily skilled artisan will understand how known data processing and data acquisition methodologies can be effectively practiced in relation to the present invention.

Figure 7:
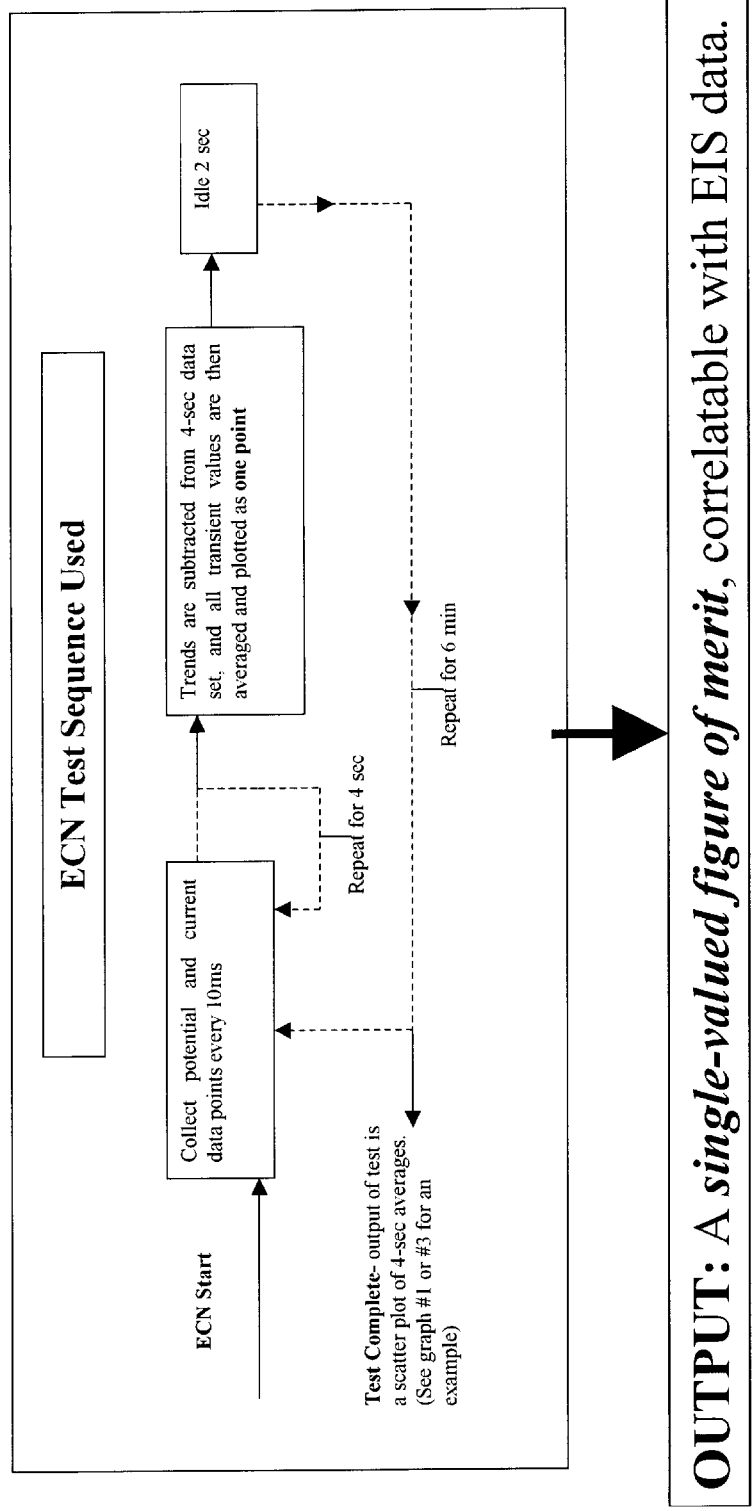
FIG. 7 is a flow diagram illustrative of ECN testing, including utilization of ECN instrumentation and data processing, which was performed by the U.S. Navy on some occasions while implementing conventional ECN apparatus and on other occasions while implementing the inventive prototype apparatus shown in FIG. 1.

Reference now being made to FIG. 7, the ECN tests conducted in this demonstration were performed as follows. Tests were run on pairs of samples for six minutes using a commercial ECN test setup. Voltage and current noise were measured using a zero-resistance ammeter (ZRA) which effectively shorts the two samples. The test solution contained within the specimens' test cells was linked with a salt bridge to allow ionic exchange. Noise data was acquired during four-second intervals every six seconds throughout the test period. Thus, the data acquisition cycle was 4 seconds "on" (data collected for 4 seconds) followed by 2 seconds "off" (no data collection for 2 seconds), repeated continuously for 6 minutes. During the 4-second acquisition period, voltage and current were measured every 10 ms. ECN tests were performed inside of a Faraday cage. Output data consisted of the average noise values for each 4-second interval plotted as a function of time.

The ECN data inventively obtained for the witness specimens and coated panels were compared to the aforementioned conventional ECN data taken on the pairs of panels. Moreover, witness specimens with freshly sanded and rusted surfaces were inventively tested to evaluate the effect of witness specimen surface condition on the ECN output. Results of initial experiments validated that ECN could indeed differentiate, as desired, between "good" and "bad" coating conditions. In general, nominal current noise values were found to vary by an order of magnitude for the two coating conditions examined. Furthermore, the initial testing demonstrated that the novel sensor setup and procedure according to this invention, in which a "witness" specimen is utilized as a probe, is feasible as a method of quantitatively assessing coating condition. Test results also showed that the presence of rust on the "witness" specimens affected the ECN data, and that nominal ECN values obtained using witness specimens were not the same as those obtained between pairs of coated panels. Overall, the prototype inventive ECN sensor was shown to function as desired, and further development and characterization of the inventive sensing method is warranted.

During some inventive testing, steel was used as the material for witness electrode 16. Instead of steel, the bare "witness" specimen, witness electrode 16, can be made of another material such as graphite or platinum or another noble metal. The term "noble metal" is generally considered to describe any of several metallic chemical elements characterized by outstanding resistance to oxidation, even at high temperatures. The "noble metal" grouping, though not strictly defined, is usually understand to include rhenium, ruthenium, rhodium, palladium, silver, osmium, iridium, platinum and gold; these elements are the metals of groups VIIb, VIII and Ib of the second and third transition series of the Periodic Table.

Figure 8:
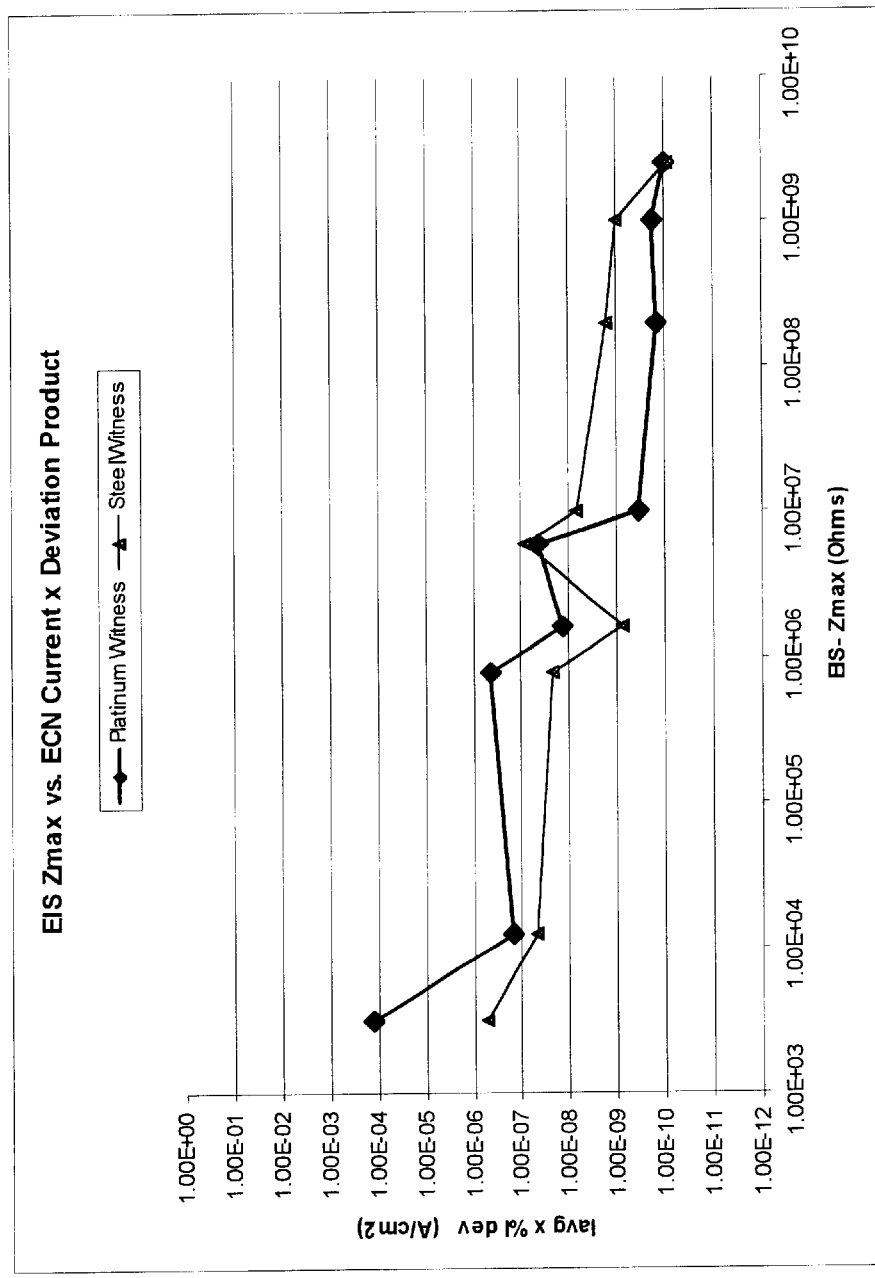
FIG. 8 is a graphical representation of correlation of an inventively obtained ECN current-deviation product (an example of a single-value figure of merit) with EIS $Z_{max}$ values for two different witness electrodes, viz., steel and platinum (Pt). As illustrated in this figure, in inventive practice, platinum is generally superior to steel as a witness material.

With reference to FIG. 8, platinum (Pt) was also used during some inventive testing, and was found to compare favorably to steel as the witness electrode 16 material. The graph in FIG. 8 illustrates the EIS $Z_{max}$ versus the ECN current-times-deviation product for two different witness electrodes 16, viz., a witness electrode 16 comprising steel and a witness electrode 16 comprising platinum. The "ECN current-deviation product" is an example of a "single-value figure of merit" which may be obtained in accordance with the present invention. As the graph in FIG. 8 suggests, for most inventive embodiments, platinum (vice steel) is the superior "witness."

An alternative method of obtaining ECN data in service was investigated by joint inventor Ruedisueli and Dr. J. N. Murray at the Naval Surface Warfare Center, Carderock Division (NSWCCD). This sub-film ECN sensor-based method involved the development and fabrication of thin-film, interdigitated steel sensors to serve as under-film ECN sensors for painted surfaces. The sensors were applied to selected locations on the bare steel interior walls of a chemical storage tank prior to painting. Upon painting the tank walls, the sensors themselves were covered with paint. By performing ECN tests on the sensors throughout the service life of the tank, differences in nominal current noise could be monitored at the sensor locations. According to this sub-film ECN sensor approach, however, the noise data is indicative of the electrochemical activity of the sensor itself rather than of the tank wall itself. Moreover, according to this sub-film ECN sensor technique, ECN testing is limited to the pre-selected areas where sensors have been installed prior to painting. Thus, this sub-film ECN sensor methodology is limited in applicability and flexibility in comparison with the inventive "witness" specimen-based ECN sensor methodology.

Another method currently under development at NSWCCD is a variation on the EIS laboratory method. According to this limited-frequency EIS approach, only the high frequency component of the measurement spectrum is utilized, thus allowing for shorter, more practical measurement times. A field-portable prototype of this limited-frequency EIS system, including a special hand-held sensor head that reportedly does not require hull (coating substrate) grounding, was nearing completion for testing as of about May 1999.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. Coating assessment apparatus suitable for on-site use in association with a metal substrate and with electrochemical noise instrumentation including an ammeter and a voltmeter, said apparatus comprising:

a receptacle for containing electrolyte and for being coupled with said metal substrate whereby said electrolyte contacts a coated portion of said metal substrate;

a witness electrode for contacting said electrolyte, said witness electrode being made of a bare single metal material;

a reference electrode for contacting said electrolyte;

a first lead means for connecting an uncoated portion of said metal substrate to said ammeter and to said voltmeter;

a second lead means for directly connecting, sans any intermediary electronic element, said witness electrode to said ammeter, said ammeter measuring the current flow between said witness electrode and said metal substrate, said current flow being approximately unimpeded between said witness electrode and said ammeter; and a third lead means for connecting said reference electrode to said voltmeter, said voltmeter measuring the potential between said reference electrode and the combination of said witness electrode and said metal substrate.

2. Coating assessment apparatus as recited in claim 1, wherein said single metal material of said witness electrode is selected from the group consisting of steel, graphite, rhenium, ruthenium, rhodium, palladium, silver, osmium, iridium, platinum and gold.

3. Coating assessment apparatus as recited in claim 1, wherein said second lead means is for directly connecting, sans any intermediary electronic element, said reference electrode to said voltmeter.

4. Coating assessment apparatus as recited in claim 1, wherein:

said receptacle has a first opening and at least a second opening;

said receptacle encloses said witness electrode and said reference electrode;

said first opening is for permitting said electrolyte, while contained by said receptacle, to contact a coated portion of said metal substrate; and said at least a second opening is for permitting the disposition of said second lead means between said witness electrode and said ammeter, and for permitting the disposition of said third lead means between said reference electrode and said voltmeter.

5. Coating assessment apparatus as recited in claim 4, further comprising coupling means, said coupling means being for coupling said receptacle with said coated metal substrate so that said electrolyte, via said first opening, contacts said coated metal substrate.

6. Coating assessment apparatus as recited in claim 5, further comprising sealing means, said sealing means being for sealing at least one of said at least a second opening so that spillage of said electrolyte is at least substantially prevented when said receptacle is coupled with said coated metal substrate.

7. Coating assessment apparatus as recited in claim 4, wherein at least one of said first opening and said at least a second opening is for permitting the introduction in said container of said electrolyte.

8. Coating assessment apparatus as recited in claim 4, further comprising injection means for infusing said electrolyte in said receptacle.

9. Coating assessment apparatus as recited in claim 4, further comprising absorbent means for retaining said electrolyte, said absorbent means being for situation in said receptacle in the vicinity of said first opening whereby said electrolyte contacts said coated portion of said metal substrate.

10. Coating assessment apparatus as recited in claim 9, wherein said absorbent means includes a structure made of a material selected from the group of materials consisting of sponge material and foam material.

11. Coating assessment apparatus as recited in claim 9, wherein said first opening is for permitting the insertion in said container of said absorbent means when said absorbent means retains said electrolyte.

12. Coating assessment apparatus as recited in claim 4, wherein:
said receptacle is at least substantially cylindrical;
said receptacle has a first end and a second end;
said opening is located at said first end; and
said at least a second opening is located at said second end.

13. Coating assessment apparatus as recited in claim 1, further comprising said electrolyte.

14. Coating assessment apparatus as recited in claim 1, wherein said ammeter is a zero resistance ammeter.

15. Coating assessment apparatus as recited in claim 1, said coating assessment apparatus further comprising processing means for calculating, based on Ohm's Law, the resistance across said coated portion of said metal substrate, wherein:
said calculating uses intermittent measurements taken by said ammeter and said voltmeter;
said resistance is calculated based on the following quotient: (the average of said intermittent measurements taken by said voltmeter) divided by (the average of said intermittent measurements taken by said ammeter); and
said calculated resistance is indicative of the quality of the coating in said coated portion of said metal substrate.

16. Coating assessment apparatus as recited in claim 15, wherein the current flow across said coated portion of said metal substrate tends to be encouraged by:
said bare single metal material of said witness electrode; and
said unimpeded current flow between said witness electrode and said ammeter.

17. A system, based on electrochemical noise, for evaluating the condition of a coating on a metallic substrate, said system comprising a zero resistance ammeter, a voltmeter, a reservoir adaptable to containment of electrolyte and to attachment to said metallic substrate whereby said electrolyte communicates with a coated portion of said metallic substrate, a witness electrode communicable with said electrolyte and at least substantially consisting of an exposed single metal material, a reference electrode communicable with said electrolyte, a first conductor for connecting an uncoated portion of said metallic substrate with said ammeter and with said voltmeter, a second conductor for connecting said witness electrode with said zero resistance ammeter in the absence of a resistor between said witness electrode and said zero resistance ammeter, and a third conductor for connecting said reference electrode with said voltmeter, wherein, upon the effecting of the respective said connections by said first conductor, said second conductor and said third conductor:
said zero resistance ammeter is capable of measuring the current between said witness electrode and said metal substrate; and
said voltmeter is capable of measuring the potential difference between said reference electrode and the coupling of said witness electrode and said metal substrate.

18. The system according to claim 17, further comprising means, associated with said ammeter and voltmeter, for acquiring, processing and storing data received from said ammeter and voltmeter.

19. The system according to claim 17, wherein said reservoir includes an at least substantially cylindrical container, wherein said container has two ends and at least one aperture at at least one said end, and wherein said reservoir is adaptable to containment of said electrolyte and to attachment to said metallic substrate whereby said communication of said electrolyte with said metallic substrate is through a said aperture.

20. The system according to claim 17, wherein said reservoir includes a container, wherein said electrolyte is a liquid which is freely containable by said container, and wherein said witness electrode and said reference electrode are each immersible in said electrolyte.

21. The system according to claim 17, wherein said reservoir includes a container and a porous member, wherein said electrolyte is liquid, wherein said container contains said porous member, wherein said porous member is at least substantially saturatable with said electrolyte, and wherein said witness electrode and said reference electrode are each communicable with said at least substantially saturatable porous member.

22. The system according to claim 17, wherein:
the circuit between said witness electrode and said metal substrate is characterized by a low resistance which is associated with:
said witness electrode essentially consisting of said exposed single metal material; and
said absence of a resistor between said witness electrode and said zero resistance ammeter; and
the respective values of said measured current and said measured voltage are high in correspondence with said low resistance characterizing said circuit between said witness electrode and said metal substrate.

23. The system according to claim 22, said system further comprising a processor capable of determining the resistance characterizing said coating on said metallic substrate, said determining being based on the average of said current measured plural times divided by the average of said current measured plural times.

24. A method, based on electrochemical noise, for evaluating the condition of a coating on a metallic substrate, said method comprising:
attaching an electrolyte reservoir to said metallic substrate whereby a coated portion of said metallic substrate is in contact with said electrolyte;
causing a witness electrode to be in contact with said electrolyte, said witness electrode at least substantially consisting of a bare single metallic material;

causing said reference electrode to be in contact with said electrolyte;

electrically connecting an uncoated portion of said metallic substrate with an ammeter and with a voltmeter;

electrically connecting said witness electrode with said ammeter so as to be at least substantially absent resistance between said witness electrode and said ammeter, said ammeter being capable of measuring the current between said witness electrode and said metallic substrate;

electrically connecting said reference electrode with said voltmeter, said voltmeter being capable of measuring the potential difference between said reference electrode and the coupling of said witness electrode and said metallic substrate;

using said ammeter for measuring plural said current values at selected intervals during a selected period of time;

using said voltmeter for measuring plural said potential difference values at said selected intervals during said selected period of time; and determining at least one resistance value indicative of said coating on said metallic substrate, said determining being based the ratio of the average of said measured voltage values to the average of said measured current values.

25. The method according to claim 24, wherein:

said electrolyte reservoir includes an at least substantially cylindrical container and said electrolyte contained thereby;

said container has two ends and at least one aperture at at least one said end; and said attaching includes rendering said contact of said metallic substrate with said metallic substrate through a said aperture.

26. The method according to claim 24, wherein said attaching includes using a magnetic ring-shaped clamp which is conformable with respect to said container and is magnetically attractive with respect to said metallic substrate.

27. The method according to claim 24 further comprising providing said electrolyte reservoir, said providing including at least partially occupying a container with liquid said electrolyte.

28. The method according to claim 27, wherein:

said at least partially occupying includes at least substantially saturating a porous member with said electrolyte and inserting said porous member in said container;

said causing said witness electrode to be in contact with said electrolyte includes causing said witness electrode to be in communication with said porous member; and said causing said reference electrode to be in contact with said electrolyte includes said reference electrode to be in communication with said porous member.

29. The method according to claim 27, wherein:

said at least partially occupying includes injecting said electrolyte into said container, thereby at least partially filling said container with said electrolyte;

said causing said witness electrode to be in contact with said electrolyte includes causing said witness electrode to be immersed in said electrolyte; and said causing said reference electrode to be in contact with said electrolyte includes causing said reference electrode to be immersed in said electrolyte.

30. The method according to claim 24, wherein said measured voltage values and said measured current values are suitably high for said determining of said at least one resistance value indicative of said coating on said metallic substrate, said suitable high measured voltage values and measured current values tending to result from:

said witness electrode at least substantially consisting of a bare single metallic material; and said resistance between said witness electrode and said ammeter being at least substantially absent.

31. Coating assessment apparatus suitable for on-site use in association with a coated metal substrate and with electrochemical noise instrumentation including an ammeter and a voltmeter, said apparatus comprising:

a receptacle for containing electrolyte and for being coupled with said coated metal substrate whereby said electrolyte contacts said coated metal substrate;

a witness electrode for contacting said electrolyte and for connecting to said ammeter;

a reference electrode for contacting said electrolyte and for connecting to said voltmeter;

a first lead means for connecting a metal portion of said coated metal substrate to said ammeter and said voltmeter;

a second lead means for directly connecting, sans any intermediary electronic element, said witness electrode to said ammeter; and a third lead means for directly connecting, sans any intermediary electronic element, said reference electrode to said voltmeter.

* * * * *